United States Patent [19]
Woodward

[11] Patent Number: 5,877,211
[45] Date of Patent: Mar. 2, 1999

[54] $EP_2$ RECEPTOR AGONISTS AS NEUROPROTECTIVE AGENTS FOR THE EYE

[75] Inventor: David F. Woodward, Lake Forest, Calif.

[73] Assignee: Allergan, Irvine, Calif.

[21] Appl. No.: 975,314

[22] Filed: Nov. 21, 1997

[51] Int. Cl.[6] .................................................. A61K 31/215
[52] U.S. Cl. ............................ 514/530; 514/573; 514/912
[58] Field of Search ....................................... 514/530, 573, 514/912

[56] References Cited

U.S. PATENT DOCUMENTS

| | | |
|---|---|---|
| 4,599,353 | 7/1986 | Bito . |
| 4,994,274 | 2/1991 | Chan et al. . |
| 5,034,413 | 7/1991 | Chan et al. . |

OTHER PUBLICATIONS

Cioffi et al, Surv. of Ophthalmol, vol. 38, 107–117, May 1994, "Microvasculature of the Anterior Optic Nerve".
Matusi et al, Nippon Rinsho, vol. 52 (8), 2158–2163, Aug. 1994, "Ophthalmological Aspects of Systemic Vasculitis".
Schwartz et al, Surv. Ophthalmol., vol. 38, 23–34, May 1994, "Ciculatory Defects of the Optic Disk and Retina in Ocular Hypertension and High Pressure Open–Angle Glaucoma".
Starr et al, Exp. Eye Research, vol. 11, 170–177, 1971, "Further Studies on the Effect of Prostaglandin on Intracular Pressure in the Rabbit".
Bito et al, 231–252, 1985, Biological Protection with Prostaglandins, "Prostaglandins and Related Compounds As Potential Ocular Therapeutic Agents".
Bito et al, Applied Pharmacology in the Medical Treatment of Glaucomas 477–505. 1984, "Prostaglandins, Other Eicosanoids, and Their Derivatives as Potential Antiglaucoma Agents".
Nilsson et al, Invest. Ophthalmol. Vis. Sci., vol. 28, 284, 1987, "$PGF_{2\alpha}$Increases Uveoscleral Outflow".
Bito et al, Arch. Ophthalmol., vol. 105, 1036–1039, Aug. 1987, "Prostaglandins, Old Concepts and New Perspectives".
Siebold et al, Prodrug 5,3, 1989, "Esterified prostaglandin shows 'potent' promise".
Nials et al, ,Cardiovascular Drug Reviews, vol. 11, No. 2, 165–179, "AH13205, A Selective Prostanoid $EP_2$–receptor Agonist".
Coleman et al, Comprehensive Medicinal Chemistry, vol. 3, 643–714, 1990, "Prostanoids and their Receptors".
Woodward et al, Prostaglandins, 371–383, 1993, "Indentification of 19(R)–OH Prostaglandin $E_2$ As A Selective Prostanoid $EP_2$–Receptor Agonist".
Chemical Abstract 123: 330038 (1995). Woodward.

*Primary Examiner*—Zohreh Fay
*Attorney, Agent, or Firm*—Robert J. Baren; Martin A. Voet; James M. Hoch

[57] ABSTRACT

The invention relates to the use of $EP_2$ receptor agonists as neuroprotective agents. In particular said compounds are represented by the formulae:

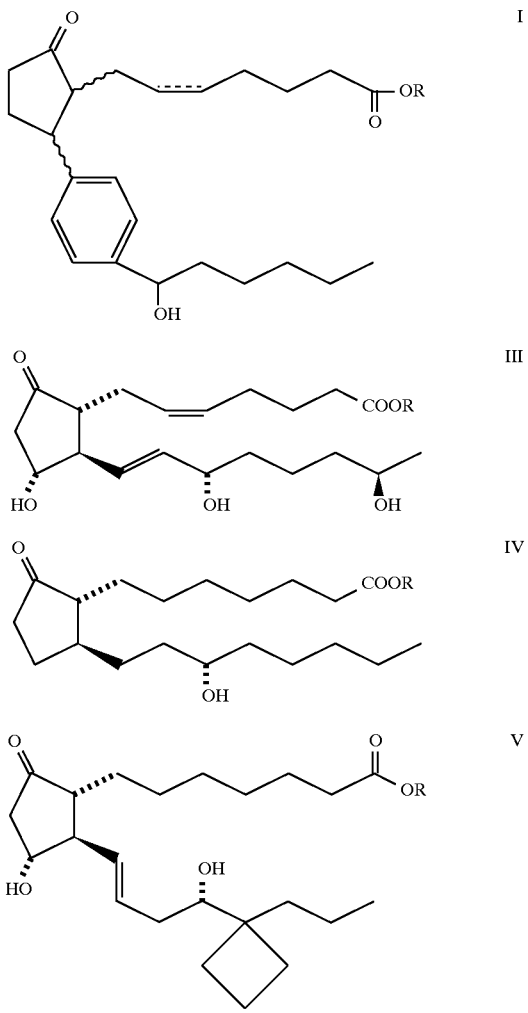

wherein the broken line attachment to the cyclopentane ring or the omega chain indicates the α configuration and the solid line attachment to the cyclopentane ring or the omega chain indicates the β configuration, R is hydrogen or a saturated or unsaturated acyclic hydrocarbon group having from 1 to about 20 carbon atoms, or —$(CH_2)_m R_1$ wherein m is 0–10, and $R_1$ is an aliphatic ring having from about 3 to about 7 carbon atoms, or an aryl or heteroaryl ring having from about 4 to about 10 carbon atoms and wherein the heteroatom is selected from the group consisting of N, O and S.

17 Claims, 2 Drawing Sheets

EP₂ RECEPTOR AGONISTS AS NEUROPROTECTIVE AGENTS FOR THE EYE

FIELD OF THE INVENTION

The present invention relates to the use of $EP_2$ receptor agonists to provide a neuroprotective effect to the eye of a mammal.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

It has long been known that one of the sequelae of glaucoma is damage to the optic nerve head. This damage, referred to as "cupping", results in depressions in areas of the nerve fiber of the optic disk. Loss of sight from this cupping is progressive and can lead to blindness if the condition is not treated effectively.

Unfortunately lowering intraocular pressure by administration of drugs or by surgery to facilitate outflow of the aqueous humor is not always effective in obviating damage to the nerves in glaucomatous conditions. This apparent contradiction is addressed by Cioffi and Van Buskirk [*Surv. of Ophthalmol.*, 38, Suppl. p. S107–16, discussion S116–17, May 1994] in the article, "Microvasculature of the Anterior Optic Nerve". The abstract states:

The traditional definition of glaucoma as a disorder of increased intraocular pressure (IOP) oversimplifies the clinical situation. Some glaucoma patients never have higher than normal IOP and others continue to develop optic nerve damage despite maximal lowering of IOP. Another possible factor in the etiology of glaucoma may be regulation of the regional microvasculature of the anterior optic nerve. One reason to believe that microvascular factors are important is that many microvascular diseases are associated with glaucomatous optic neuropathy.

Subsequent to Cioffi, et al., Matusi published a paper on the "Ophthalmologic aspects of Systemic Vasculitis" [*Nippon Rinsho*, 52 (8), p. 2158–63, August 1994] and added further support to the assertion that many microvascular diseases are associated with glaucomatous optic neuropathy. The summary states:

Ocular findings of systemic vasculitis, such as polyarteritis nodosa, giant cell angitis and aortitis syndrome were reviewed. Systemic lupus erythematosus is not categorized as systemic vasculitis, however its ocular findings are microangiopathic. Therefore, review of its ocular findings was included in this paper. The most common fundus finding in these diseases is ischemic optic neuropathy or retinal vascular occlusions. Therefore several points in diagnosis or pathogenesis of optic neuropathy and retinal and choroidal vaso-occlusion were discussed. Choroidal ischemia has come to be able to be diagnosed clinically, since fluorescein angiography was applied in these lesions. When choroidal arteries are occluded, overlying retinal pigment epithelium is damaged. This causes disruption of barrier function of the epithelium and allows fluid from choroidal vasculatures to pass into subsensory retinal spaces. This is a pathogenesis of serous detachment of the retina. The retinal arterial occlusion formed non-perfused retina. Such hypoxic retina released angio-genesis factors which stimulate retinal and iris neovascularizations and iris neovascularizations may cause neovascular glaucoma.

B. Schwartz, in "Circulatory Defects of the Optic Disk and Retina in Ocular Hypertension and High Pressure Open-Angle Glaucoma" [*Surv. Ophthalmol.*, 38, Suppl. pp. S23–24, May 1994] discusses the measurement of progressive defects in the optic nerve and retina associated with the progression of glaucoma. He states:

Fluorescein defects are significantly correlated with visual field loss and retinal nerve fiber layer loss. The second circulatory defect is a decrease of flow of fluorescein in the retinal vessels, especially the retinal veins, so that the greater the age, diastolic blood pressure, ocular pressure and visual field loss, the less the flow. Both the optic disk and retinal circulation defects occur in untreated ocular hypertensive eyes. These observations indicate that circulatory defects in the optic disk and retina occur in ocular hypertension and open-angle glaucoma and increase with the progression of the disease.

Thus, it is evident that there is an unmet need for agents that have neuroprotective effects in the eye that can stop or retard the progressive damage that occurs to the nerves as a result of glaucoma or other ocular afflictions.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M. S. *Exp. Eye Res.* 1971, 11, pp. 170–177; Bito, L. Z *Biological Protection with Prostaglandins* Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505). Such prostaglandins include $PGF_{2\alpha}$, $PGF_{1\alpha}$, $PGE_2$, and certain lipid-soluble esters, such as $C_1$ to $C_5$ alkyl esters, e.g. 1-isopropyl ester, of such compounds.

In the U.S. Pat. No. 4,599,353 certain prostaglandins, in particular $PGE_2$ and $PGF_{2\alpha}$ and the $C_1$ to $C_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uveoscleral outflow [Nilsson et al., *Invest. Ophthalmol. Vis. Sci.* 2 8(suppl), 284 (1987)].

The isopropyl ester of $PGF_{2\alpha}$ has been shown to have significantly greater hypotensive potency than the parent compound, which was attributed to its more effective penetration through the cornea. In 1987 this compound was described as "the most potent ocular hypotensive agent ever reported." [See, for example, Bito, L. Z., *Arch. Ophthalmol.* 105, 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potential of prostaglandins in the management of conditions associated with increased ocular pressure, e.g. glaucoma, is greatly limited by these side effects.

Certain phenyl and phenoxy mono, tri and tetra nor prostaglandins and their 1-esters are disclosed in European Patent Application 0,364,417 as useful in the treatment of glaucoma or ocular hypertension.

In a series of co-pending United States patent applications assigned to Allergan, Inc. prostaglandin esters with increased ocular hypotensive activity accompanied by no or substantially reduced side-effects are disclosed. The co-pending U.S. Ser. No. 386,835 (filed 27 Jul. 1989), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 357,394 (filed 25 May 1989). Similarly, 11,15-9,15- and 9,11-diesters of prostaglandins, for example 11,15-dipivaloyl $PGF_{2\alpha}$ are known to have ocular hypotensive activity. See the co-pending patent applications U.S. Ser. No. 385,645 filed 27 Jul. 1990, now U.S. Pat. No. 4,494,274; U.S. Ser. No. 584,370 which is a continuation of U.S. Ser. Nos. 386,312, and 585,284, now U.S. Pat. No. 5,034,413 which is a continuation of U.S. Ser. No. 386,834, where the parent applications were filed on 27 Jul. 1989. The disclosures of these patent applications are hereby expressly incorporated by reference.

Finally, certain $EP_2$-receptor agonists are disclosed in Nials et al, *Cardiovascular Drug Reviews*, Vol. 11, No. 2, pp. 165–179, Coleman et al, *Comprehensive Medicinal Chemistry*, Vol. 3, pp. 643–714, 1990 and Woodward et al, *Prostaglandins*, pp. 371–383, 1993.

SUMMARY OF THE INVENTION

We have found that $EP_2$-receptor agonists are potent neuroprotective agents. We have further found that (±) trans-2-[-4(1-hydroxyhexyl)phenyl]-5-oxocyclopentaneheptanoicacid, and certain other $EP_2$-receptor agonists, described below, and ester and unsaturated derivatives thereof, are especially useful in providing a neuroprotective effect to the eye of a mammal, e.g. a human.

The present invention relates to methods of providing a neuroprotective effect to the eye of a mammal, e.g. a human, which comprises administering an effective amount of a compound represented by the formula I

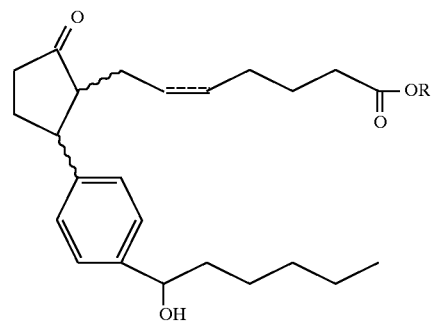

wherein, the wavy bands indicate the α or β configuration, R is hydrogen or a saturated or unsaturated acyclic hydrocarbon group having from 1 to about 20 carbon atoms, or —$(CH_2)_m R_1$ wherein m is 0–10, and $R_1$ is an aliphatic ring having from about 3 to about 7 carbon atoms, or an aryl or heteroaryl ring having from about 4 to about 10 carbon atoms, e.g. $R_1$ may be cyclohexyl, phenyl, thienyl, pyridyl or furanyl, or a pharmaceutically acceptable salt thereof and the dashed bond represents either a single or double bond which may be in the cis or trans position. Preferably $R_1$ is lower alkyl.

More preferably the method of the present invention comprises administering a compound represented by the formula II

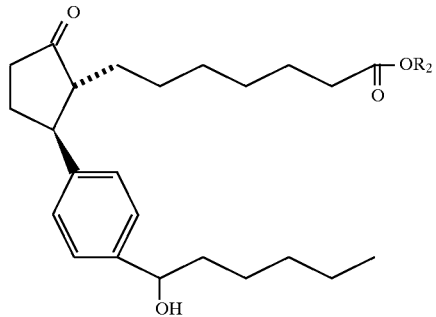

wherein $R_2$ is hydrogen or a lower alkyl radical and the other symbols are as defined above.

BRIEF DESCRIPTION OF THE DRAWING FIGURES

FIGS. 1A through 1D show a comparison of the neuroprotective effects of $EP_2$ agonists, e.g. see FIGS. 1C and 1D, with prostaglandins having no $EP_2$ agonist activity, e.g. see FIGS. 1A and 1B, in preventing neuronal damage.

DETAILED DESCRIPTION OF THE INVENTION

Figure 1A:
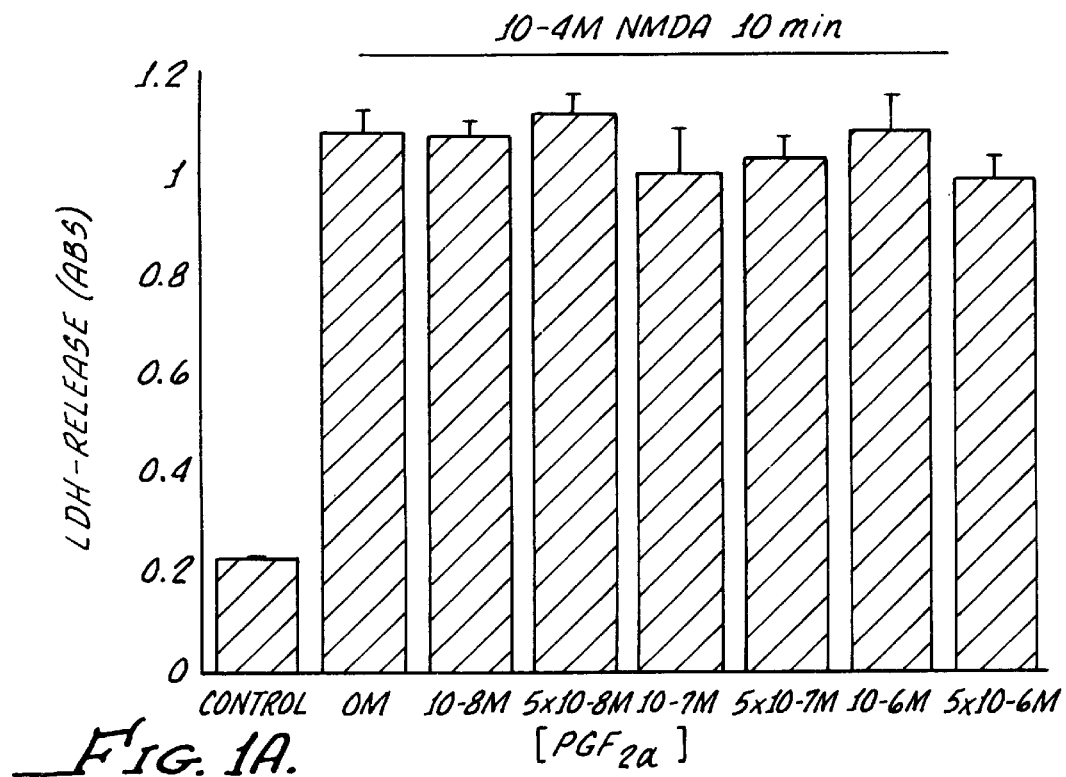
Figure 1B:
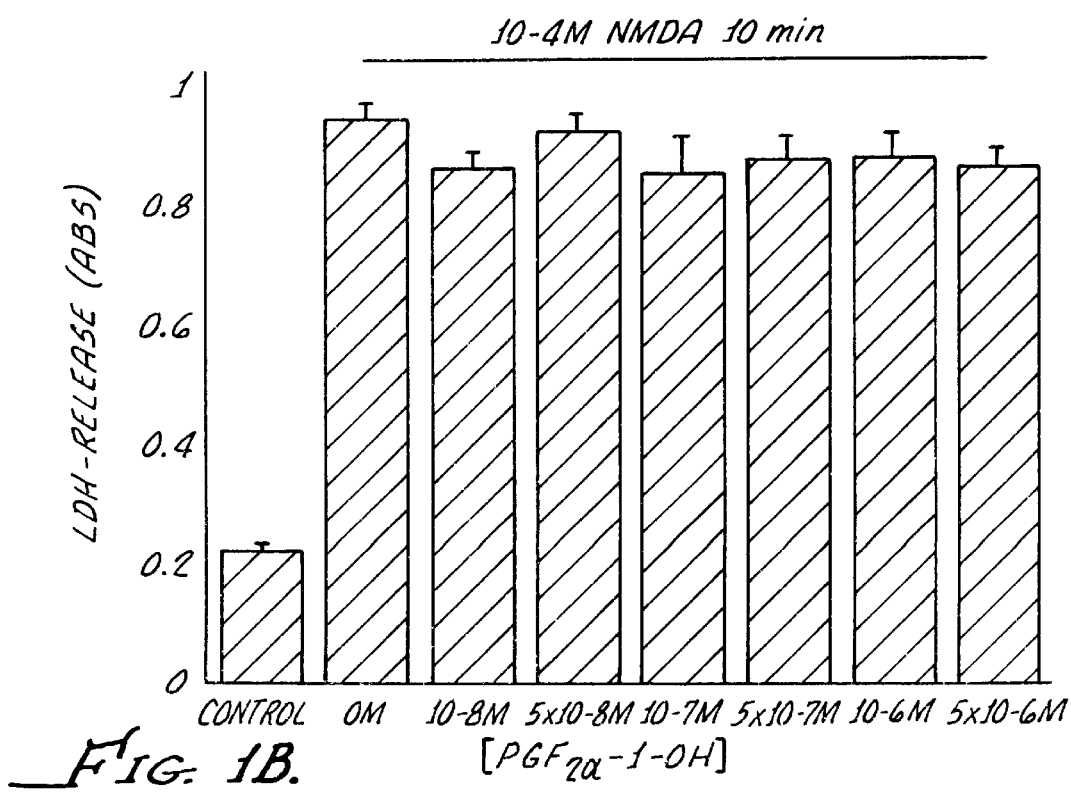
Figure 1C:
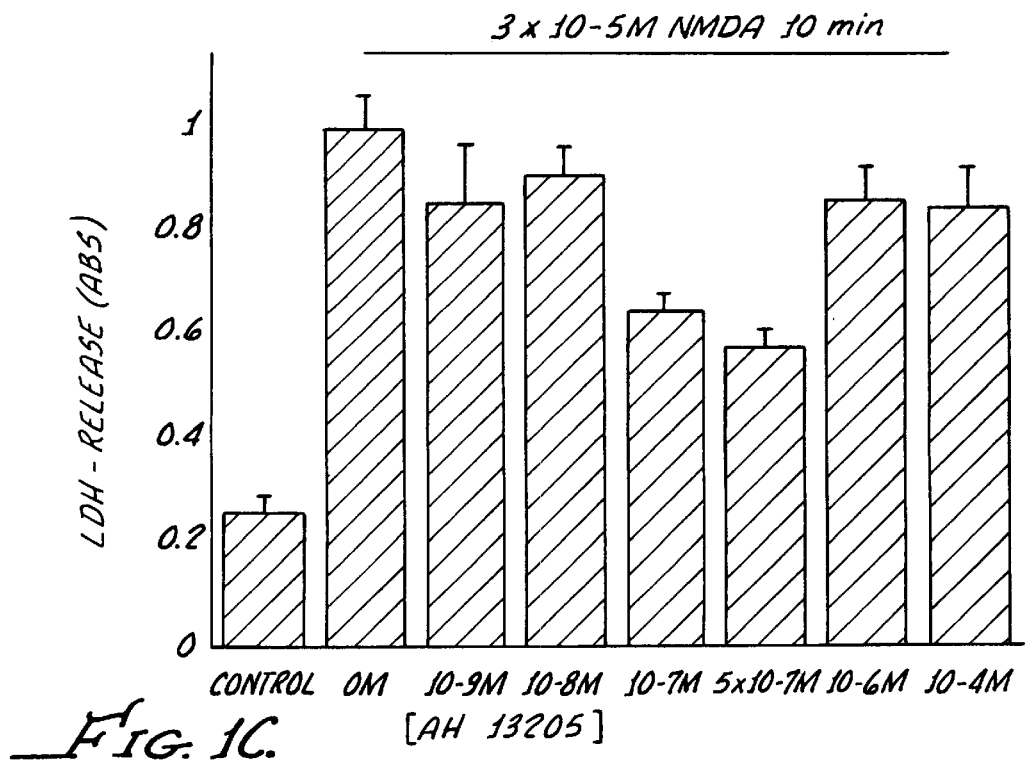
Figure 1D:
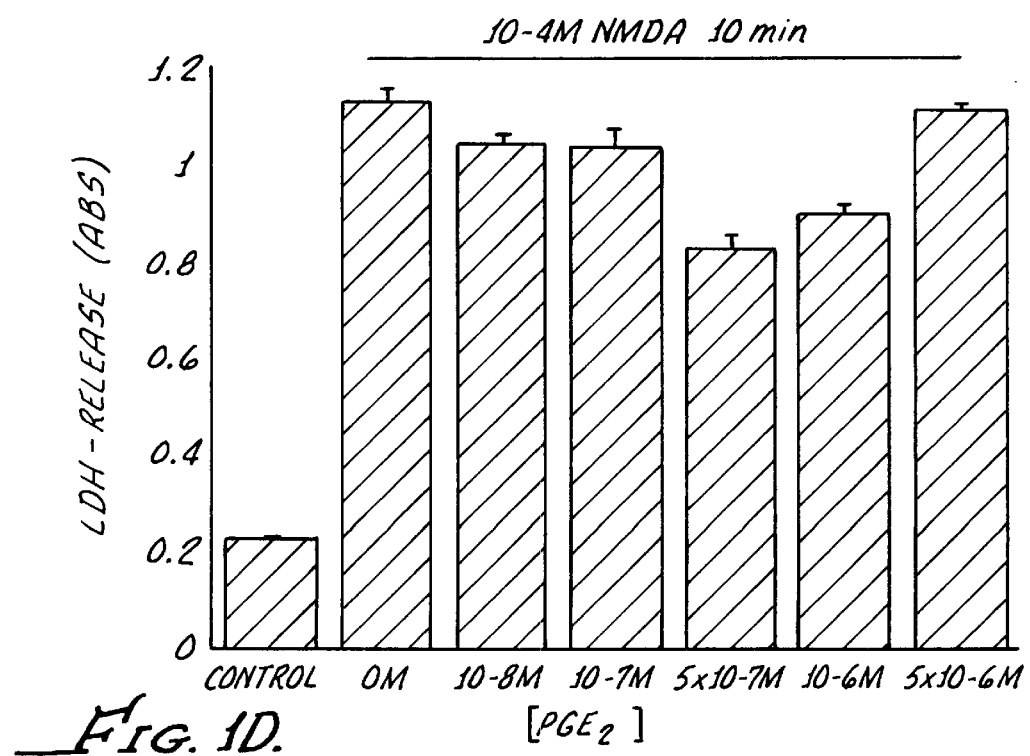

The present invention relates to the use of (±) trans-2-[-4(1-hydroxyhexyl)phenyl]-5-oxocyclopentaneheptanoicacid, and ester and unsaturated derivatives thereof as neuroprotective agents. These therapeutic agents are represented by compounds having the formula I

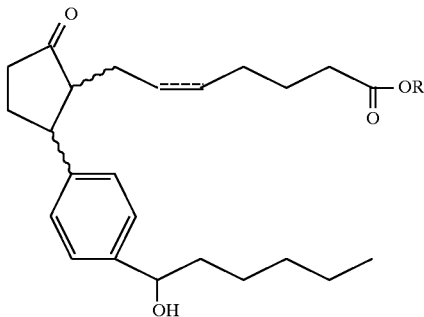

as defined above. The preferred compounds used in accordance with the present invention are encompassed by the following structural formula II

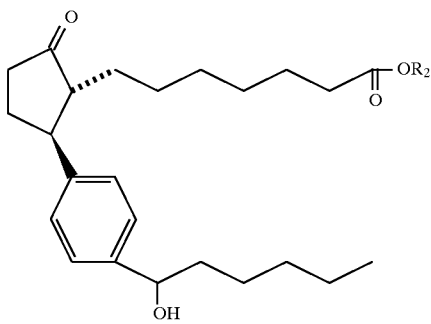

wherein $R_2$ is hydrogen or a lower alkyl radical.

In all of the above formulae, as well as in those provided hereinafter, the straight lines represent bonds. Where there is no symbol for the atoms between the bonds, the appropriate carbon-containing radical is to be inferred. For example in formula I, the radical between the cyclopentyl ring and the

radical is a polymethylene $(CH_2)$ radical, i.e. a hexylenyl radical. The dotted lines on the bond between carbons 5 and 6 (C-5), indicate a single or a double bond which can be in the cis or trans configuration. The radical adjacent to the double bond is a CH radical. If two solid lines are used that indicates a specific configuration for that double bond. Hatched lines at positions C-9 and C-11 indicate the α configuration. If one were to draw the β configuration, a solid triangular line would be used.

In the compounds used in accordance with the present invention, compounds having the C-9 or C-11 substituents in the α or β configuration are contemplated. In all formulas provided herein, broken line attachments to the cyclopentane ring or the omega chain indicate substituents in the α configuration. Thickened solid line attachments to the cyclopentane ring or the omega chain indicate substituents in the β configuration.

For the purpose of this invention, unless further limited, the term "alkyl" refers to alkyl groups having from one to ten carbon atoms and includes "lower alkyl" radicals having from one to five carbon atoms, the term "cycloalkyl" refers to cycloalkyl groups having from three to seven carbon atoms, the term "aryl" refers to aryl groups having from four to ten carbon atoms. The term "saturated or unsaturated acyclic hydrocarbon group" is used to refer to straight or branched chain, saturated or unsaturated hydrocarbon groups having from one to about six, preferably one to about four carbon atoms. Such groups include alkyl, alkenyl and alkynyl groups of appropriate lengths, and preferably are alkyl, e.g. methyl, ethyl, propyl, butyl, pentyl, or hexyl, or an isomeric form thereof.

The definition of R may include a cyclic component, $-(CH_2)_m R_1$, wherein m is 0–10, $R_2$ is an aliphatic ring from about 3 to about 7 carbon atoms, or an aromatic or heteroaromatic ring. The "aliphatic ring" may be saturated or unsaturated, and preferably is a saturated ring having 3–7 carbon atoms, inclusive. As an aromatic ring, $R_1$ preferably is phenyl, and the heteroaromatic rings have oxygen, nitrogen or sulfur as a heteroatom, i.e., $R_1$ may be thienyl, furanyl, pyridyl, etc. Preferably m is 0–4.

Preferred representatives of the compounds within the scope of the present invention are (±) trans-2-[-4(1-hydroxyhexyl)phenyl]-5-oxocyclopentaneheptanoicacid, unsaturated derivatives thereof, and lower alkyl esters of these compounds.

A compound which may be used in the pharmaceutical compositions and the methods of treatment of the present invention is (±) trans-2-[-4(1-hydroxyhexyl)phenyl]-5-oxocyclopentaneheptanoicacid.

A pharmaceutically acceptable salt is any salt which retains the activity of the parent compound and does not impart any deleterious or undesirable effect on the subject to whom it is administered and in the context in which it is administered. Such salts are those formed with pharmaceutically acceptable cations, e.g., alkali metals, alkali earth metals, etc.

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 0–10 |
| buffer | 0.01–10 |
| pH adjustor | q.s. pH 4.5–8.0 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations for use in the method of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20–35 $\mu$l.

The invention is further illustrated by the following non-limiting Examples.

EXAMPLE 1

(±) Trans-2-[-4(1-hydroxyhexyl)phenyl]-5-oxocyclo-pentaneheptanoicacid and Lower Alkyl Esters Thereof The above acid compound is well known and may be purchased or synthesized by methods known in the art. The lower alkyl esters of this compound may be made by the esterification procedures described in the various patent applications described in the Background of the Invention.

EXAMPLE 2

Method of Measuring a Neuroprotective Effect

The dissection and dissociation of the rat hippocampal neuron cell cultures was carried out. Briefly, whole cerebral neocortices were removed from fetal rats, gestation age 15–19 days and kept in calcium-, magnesium-free Hanks' balanced salt solution. The hippocampi were removed under a dissecting microscope and the meninges were stripped away. When all the hippocampi were removed, the tissues were incubated in 0.05% trypsin solution for 30 minutes at 37° C. At the end of 340 minutes, the trypsin solution was replaced with plating medium (minimal essential medium supplemented with 2% Hyclone horse serum, 1% fetal calf serum, 25 mM glucose, 1% glutamine and 1% penicillin/streptomycin and $N_2$ supplement). Then the tissues were triturated with a Pasteur pipette 10 times and then again with a pipette whose tip has been fire polished to about half the normal diameter. The dissociated neuronal cells then were plated on poly D-lysine coated, 15 mm 24 well plates ($2\times10^5$ cells/well) in plating medium.

The cell cultures were kept at 37° C. in a humidified, 5% $CO_2$-containing atmosphere. After 1–2 days, the horse serum level in the plating media was increased to 8%. After 4–7 days, the non-neuronal cell division was halted by 24 hours exposure to $10^{-6}$M Cytosine arabinoside (ARA-C), and the cells were then placed into growing medium with 4% horse serum, 1% fetal calf serum, 25 mM glucose, 1% glutamine and 1% penicillin/streptomycin and $N_2$ supplement. Subsequent medium replacement was carried out every other day until the neuronal cells matured (15–20 days). Only matured cell cultures were selected for study.

Exposure of the excitatory amino acids was performed in minimal essential medium (MEM). Extreme care was taken to wash out the growing medium from cultures before the addition of the excitatory amino acid since the neurons are very sensitive to disturbance. Matured cell cultures were exposed to either glutamate, $\alpha$-amino-3-hydroxy-5-methyl-4-isoxazole propionic acid (AMPA), N-methyl-D-aspartate (NMDA), or kainic acid.

Cytotoxicity or cell injury was scored by light microscopy examination with trypan blue. In most experiments, the overall neuronal cell injury was quantitated by the amount of lactate dehydrogenase (LDH) released by the damaged cells into the media 24 hours after drug exposure.

LDH was measured at room temperature using Promega non-radioactive cytotoxicity assay kit. The absorbance of the reaction mixture was measured at 490 nm.

The Figure shows examples of LDH release after exposure of different exitotoxins and their antagonists.

As shown in the Figure, the effects of the $EP_2$ agonist AH 13205 on NMDA-induced neurotoxicity is shown in the top right panel. It is noted that $PGF_{2\alpha}$ and $PGF_{2\alpha}$ 1-OH are inactive, thereby indicating that this is a specific $EP_2$ receptor mediated effect.

EXAMPLE 3

Determination of $EP_2$ Receptor Activity $EP_2$ receptor activity may be measured in accordance with the procedure disclosed in Woodward et al, *Prostaglandins*, pp. 371–383, 1993, which is hereby incorporated by reference in its entirety.

EXAMPLE 4

Method of Measuring a Neuroprotective Effect

The Experiment of Example 2 is repeated with other $EP_2$ Agonists, i.e. 19 (R)-OH $PGE_2$, AY 23626 and methyl 9-keto-11$\alpha$,15$\alpha$-dihydroxy-16,16 trimethyleneprosta-13- transenoate (butaprost) and the results are essentially as shown in the Figure for AH 13205.

19 (R)-OH PGE$_2$, AY 23626 and butaprost have the following structures, respectively.

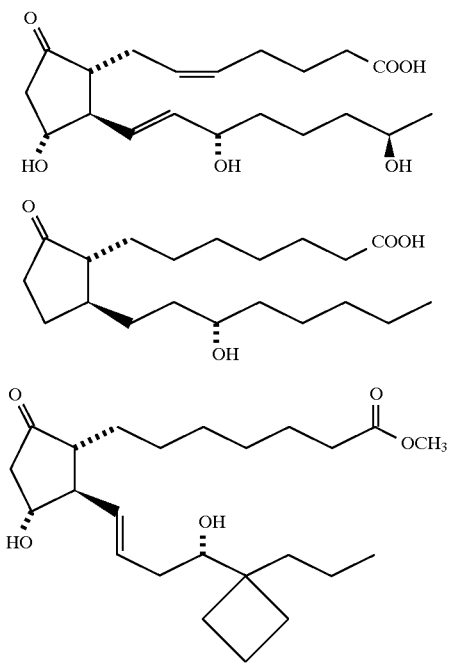

However, as with (±) trans-2-[-4(1-hydroxyhexyl)phenyl]-5-oxocyclopentaneheptanoicacid, the corresponding 1-ester or, in the case of butaprost other 1-ester derivatives as well as the 1-acid derivative are also useful in the method of the present invention.

The foregoing description details specific methods and compositions that can be employed to practice the present invention, and represents the best mode contemplated. However, it is apparent from one of ordinary skill in the art that different pharmaceutical compositions may be prepared and used with substantially the same results. That is, other EP$_2$-receptor agonists, will effectively lower intraocular pressure in animals and are within the broad scope of the present invention.

I claim:

1. A method of providing a neuroprotective effect to the eye of a mammal not having higher than normal intraocular pressure (IOP) which comprises applying to the eye an amount sufficient to treat ocular hypertension of a compound of formula I, III, IV or V

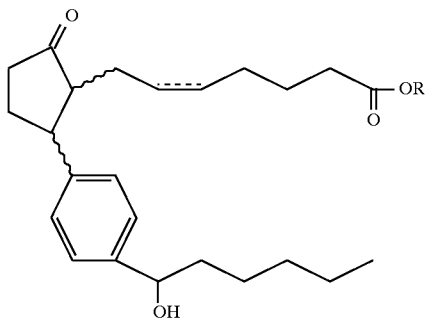

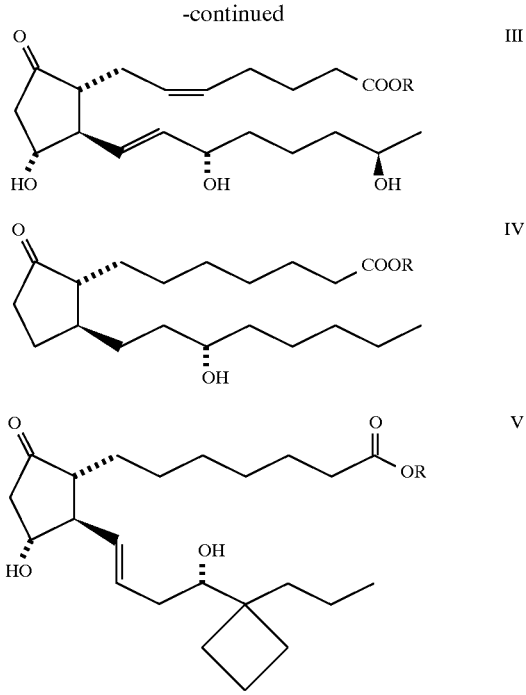

wherein the broken line attachment to the cyclopentane ring or the omega chain indicates the α configuration and the solid line attachment to the cyclopentane ring or the omega chain indicates the β configuration, R is hydrogen or a saturated or unsaturated acyclic hydrocarbon group having from 1 to about 20 carbon atoms, or —(CH$_2$)$_m$R$_1$ wherein m is 0–10, and R$_1$ is an aliphatic ring having from about 3 to about 7 carbon atoms, or an aryl or heteroaryl ring having from about 4 to about 10 carbon atoms and wherein the heteroatom is selected from the group consisting of N, O and S.

2. The method of claim 1 wherein said compound is a prostaglandin derivative of the formula II, VI, VII or VIII

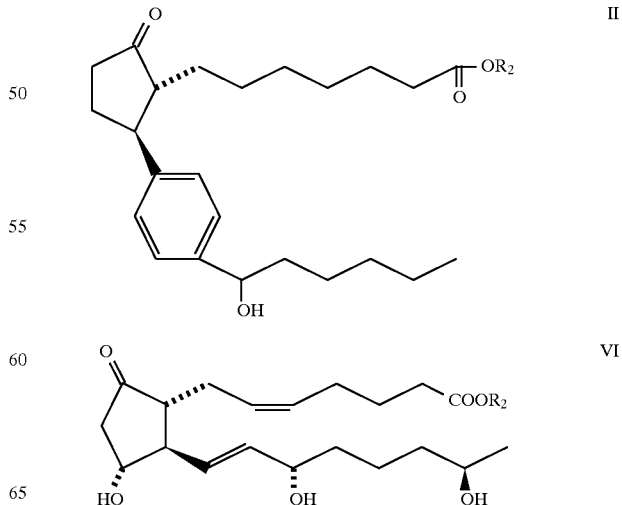

-continued

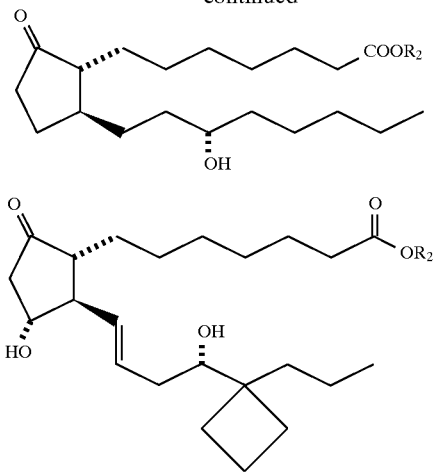

wherein R₂ is a hydrogen or a lower alkyl radical.

3. The method of claim 2 wherein said compound is

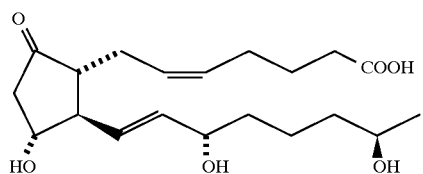

4. The method of claim 2 wherein said compound is

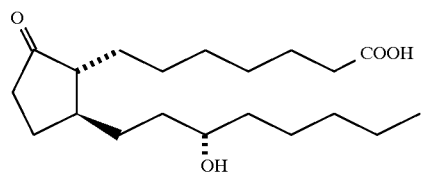

5. The method of claim 2 wherein said compound is

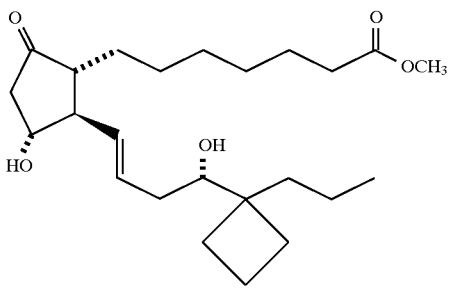

6. The method of claim 2 wherein said compound is

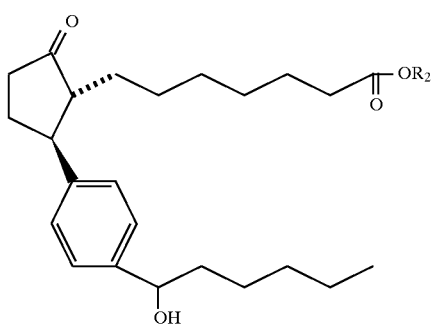

wherein R₂ is hydrogen or a lower alkyl radical.

7. A method for providing a neuroprotective effect to the eye of a mammal not having higher than normal intraocular pressure (IOP) which comprises applying to the eye an amount sufficient to treat ocular hypertension of a compound having $EP_2$ receptor agonist activity.

8. A method of protecting the retinal or optic nerve cells in a mammal not having higher than normal intraocular pressure (IOP) suffering a noxious action or at risk of experiencing a noxious action on said nerve cells comprising administering to said mammal an effective amount of a compound of formula I, III, IV or V to inhibit or prevent nerve cell injury or death

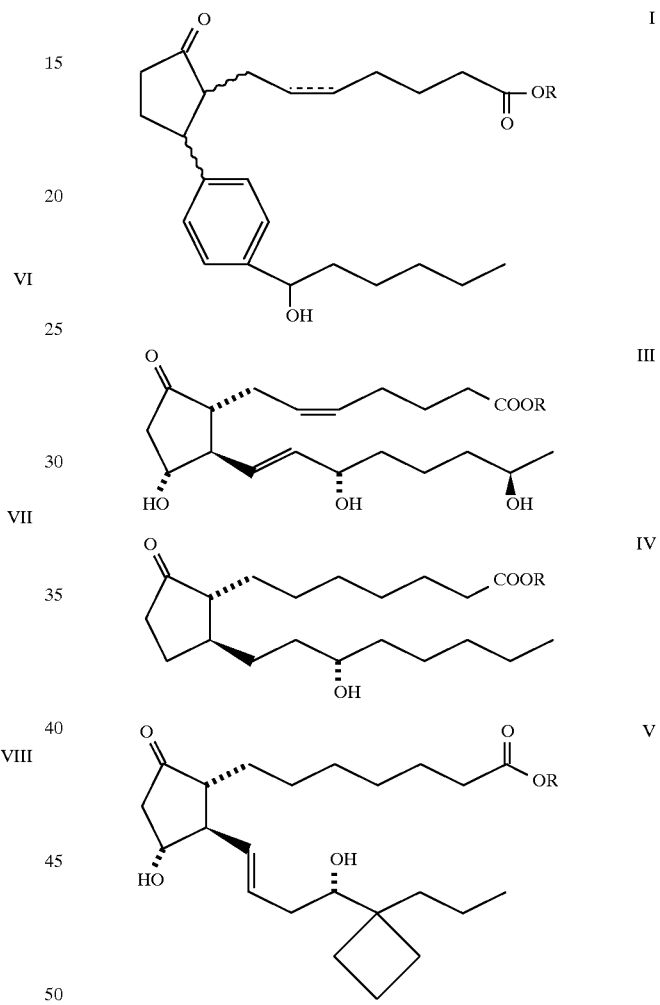

wherein the broken line attachment to the cyclopentane ring or the omega chain indicates the α configuration and the solid line attachment to the cyclopentane ring or the omega chain indicates the β configuration, R is hydrogen or a saturated or unsaturated acyclic hydrocarbon group having from 1 to about 20 carbon atoms, or —$(CH_2)_m R_1$ wherein m is 0–10, and $R_1$ is an aliphatic ring having from about 3 to about 7 carbon atoms, or an aryl or heteroaryl ring having from about 4 to about 10 carbon atoms and wherein the heteroatom is selected from the group consisting of N, O and S.

9. The method of claim 8 wherein the noxious action is the elevated intraocular pressure of glaucoma.

10. The method of claim 8 wherein the noxious action is ischemia associated with glaucoma.

11. The method of claim 8 wherein the noxious action is diabetic retinopathy.

12. The method of claim 8 wherein the noxious action is non-glaucomatous ischemia.

13. The method of claim 8 wherein the noxious action is microangiopathic in nature and is a symptom of the disease chosen from the group consisting of polyarteritis nodosa, giant cell angitis, aortitis syndrome and systemic lupus erythematosus.

14. The method of claim 8 wherein oral administration is used to supply the compound to the mammal systemically.

15. The method of claim 8 wherein intrabulbar injection in the eye is used to supply the compound to the mammal.

16. The method of claim 8 wherein parenteral administration is used to supply the compound to the mammal systemically.

17. The method of claim 8 wherein intramuscular injection is used to supply the compound to the mammal systemically.

\* \* \* \* \*